United States Patent [19]
Isogai et al.

[11] Patent Number: 4,650,911
[45] Date of Patent: Mar. 17, 1987

[54] PROCESS FOR PRODUCING ETHANOL

[75] Inventors: Nobuo Isogai; Motoyuki Hosokawa; Takashi Okawa; Natsuko Wakui; Toshiyasu Watanabe, all of Niigata, Japan

[73] Assignee: S. Ishizaka, President of Agency of Industrial Science and Technology, Tokyo, Japan

[21] Appl. No.: 858,521

[22] Filed: Apr. 21, 1986

Related U.S. Application Data

[63] Continuation of Ser. No. 503,900, Jun. 13, 1983, abandoned.

[30] Foreign Application Priority Data

Jun. 16, 1982 [JP] Japan .................................. 57-102145

[51] Int. Cl.4 ........................ C07C 29/00; C07C 31/08
[52] U.S. Cl. ..................................................... 568/902
[58] Field of Search ..................................... 568/902 H

[56] References Cited

U.S. PATENT DOCUMENTS 4,126,752 11/1978 Novotny et al. ..................... 568/902
4,386,009 5/1983 Feder et al. .......................... 568/902
4,393,255 7/1983 Mitchell et al. ..................... 568/902

FOREIGN PATENT DOCUMENTS 2036739 7/1980 United Kingdom ................ 568/902

Primary Examiner—J. E. Evans
Attorney, Agent, or Firm—Browdy and Neimark

[57] ABSTRACT

A process for producing ethanol which comprises reacting methanol, carbon monoxide and hydrogen in the presence of (a) a catalyst containing a cobalt component, an iron component, a ruthenium component and an iodine component, (b) at least one organic solvent and (c) water, said catalyst comprising the cobalt component in amount of 0.1–500 milligram atom (mg-atom) in terms of cobalt per 1 mol of methanol, an iron component in amount of 0.01–4 atoms per 1 atom of cobalt in terms of metal, a ruthenium component in amount of 0.01–4 atoms per 1 atom of cobalt in terms of metal and an iodine component in amount of 0.05–20 atoms per 1 atom of cobalt is disclosed. According to the present invention, selectivity to ethanol is high and ethanol can be obtained under mild conditions.

10 Claims, No Drawings

PROCESS FOR PRODUCING ETHANOL

This application is a continuation of application Ser. No. 503,900, filed 6/13/1983, now abandoned.

BACKGROUND OF THE INVENTION

This invention relates to a process for producing ethanol from methanol, carbon monoxide and hydrogen, selectively.

It was known in the prior art that ethanol was produced from methanol, carbon monoxide and hydrogen by using a catalyst comprising a cobalt component or a iodine or bromine component and optionally a ruthenium component, an osmium component and a ligand. For example, Japanese Patent Publication (kokoku) No. 24863/1963 discloses a process for producing ethanol which comprises reacting methanol, carbon monoxide and hydrogen in the presence of a cobalt catalyst and an iodine co-catalyst. U.S. Pat. No. 3,285,948 discloses a process for producing ethanol which comprises reacting methanol, carbon monoxide and hydrogen in the presence of a catalyst comprising a soluble cobalt compound, iodine or an iodine compound and a ruthenium compound.

Recently, it has been proposed to add a variety of ligands, such as tertiary phosphine, tertiary arsines or tertiary antimony to the prior catalyst for producing ethanol from methanol, carbon monoxide and hydrogen. For example, British Pat. No. 1,546,428 discloses a process for producing ethanol by reacting methanol, carbon monoxide and hydrogen in a hydrocarbon solvent in the presence of the catalyst composed of cobalt-halide-tertiary phosphine.

Japanese Patent Publication (kokai) No. 49326/1980 discloses a multidentate ligand containing cobalt-bromine or iodine-nitrogen or phosphorus atom as such catalyst.

British Pat. No. 2,036,739 discloses a process for producing ethanol by reacting methanol, carbon monoxide and hydrogen in the presence of a catalyst composed of cobalt and a metal of Group VIII of the Periodic Table (Fe, Ru, Os, Rh, Ir, Ni, Pd and Pt), promoter composed of a tertiary phosphine, a tertiary arsine or a tertiary antimony and iodide or bromine.

Japanese Patent Publication (kokai) No. 92330/1980 discloses a catalyst comprising hydride cobalt carbonyl complex, iodine, a ruthenium compound and a tertiary phosphine, a tertiary antimony or a tertiary arsine as such catalyst.

U.S. Pat. No. 4,233,466 discloses a catalyst for production of ethanol from methanol, carbon monoxide and hydrogen which comprises cobalt, ruthenium, iodine and a tertiary phosphine in which a molar ratio of phosphorus to iodine is between 1:0.36–1:5 and a molar ratio of phosphrus to cobalt is more than 1.5.

However, when methanol is reacted with carbon monoxide and hydrogen in the presence of any one of these known catalysts on an industrial scale, by-products, such as dimethyl ether, methyl ethyl ether, diethyl ether, acetaldehyde, dimethoxy ethane, acetic acid, methyl formate, methyl acetate, ethyl acetate and other compounds of $C_2$ or more other than ethanol (object product) are formed, so selectivity to neat ethanol is low. Catalysts containing ligands have a variety of shortcomings.

On the other hand, Japanese Patent Publication (kokoku) No. 24863/1963 or U.S. Pat. No. 3,285,948 discloses a process for producing ethanol which comprises reacting methanol, carbon monoxide and hydrogen at a temperature of 175°–230° C. and a pressure of more than 281 Kg/cm$^2$G in the presence of a catalyst comprising cobalt-iodine or a catalyst comprising cobalt-iodine-ruthenium and in the absence of any solvent. Since the catalysts do not contain any ligands, it is easy to handle them. However, when the above catalysts are used, by-products, such as ethers and methyl acetate are formed in a large amount, so selectivity to neat ethanol becomes lower extremely.

When a catalysts comprising cobalt-iodine or cobalt-iodine-ruthenium and a ligand are used, formation of by-product, such as ethers are suppressed. However, since the catalysts contain ligands, activity of the catalysts are lowered. Therefore, in case of using catalysts containing ligands, the reaction must be carried out at a higher temperature. This results in forming by-products and lowering selectivity to ethanol. Particularly, the catalysts contain cobalt and ruthenium as well as iodine or bromine and ligands, such as a tertiary phosphine, a tertiary antimony or a tertiary arsine as a ligand, so the following shortcomings are produced in case of carrying out the reaction in the presence of the catalyst on a commercial base:

Since ligands, such as a tertiary phosphine are instable to heat, the ligands are likely to be decomposed in the reaction system, or quality of the ligands is likely to be changed. Therefore, it is difficult to recover the active catalysts from the system. In addition, recovery of each component constituting the catalysts not only need complicated operation, but also loss of the catalysts are great in recovery of the catalysts. Since the catalysts are costly, loss of the catalysts are unpreferablly in case of recovering the catalysts.

In the prior processes, there were problem in respect of selectivity to ethanol, reaction speed and recovery of the catalyst. The prior processes are not industrially satisfactory.

SUMMARY OF THE INVENTION

The present inventors carried out research for overcoming the shortcomings mentioned above. As a result we found that when methanol reacts with carbon monoxide and hydrogen in the presence of (a) a catalyst containing a cobalt component, an iron component, a ruthenium component and an iodine component, (b) an organic solvent and (c) water, ethanol is produced in high selectivity to ethanol.

This invention relates to a process for producing ethanol which comprises reacting methanol, carbon monoxide and hydrogen in the presence of (a) a catalyst containing a cobalt component, and iron component, a ruthenium component and an iodine compound (b) an organic solvent and (c) water, said catalyst comprising the cobalt component in amount of 0.1–500 milligram atom (mg-atom) in terms of cobalt per 1 mol of methanol, an iron component in amount of 0.01–4 atoms per 1 atom of cobalt in terms of metal, a ruthenium component in amount of 0.01–4 atoms per 1 atom of cobalt in terms of metal and an iodine component in amount of 0.05–20 atoms per 1 atom of cobalt.

DETAILED DESCRIPTION OF THE INVENTION

The catalysts employed in the present invention contain a cobalt component, a ruthenium component, an iron component and an iodine component. The cobalt component, the ruthenium component and the iron component include metallic cobalt or cobalt compounds, metallic ruthenium or ruthenium compounds and metallic iron or iron compounds, respectively.

Cobalt compounds include, for example, cobalt iodides, cobalt bromides, cobalt chlorides, cobalt oxides, cobalt carbonates, cobalt formates, cobalt acetates, cobalt naphthenates, cobalt acetylacetonates, cobalt carbonyls and the like.

Iron compounds include, for example, iron iodides, iron chlorides, iron oxides, iron acetates, iron acetylacetonates, iron carbonyls and the like.

The ruthenium compounds include, for example, ruthenium iodides, ruthenium chlorides, ruthenium bromides, ruthenium hydroxides, ruthenium acetates, ruthenium carbonyls and the like.

The iodine components include iodine or iodine compounds.

The iodine compounds include, for example, hydrogen iodide, methyl iodide, sodium iodide, potassium iodide, calcium iodide, lithium iodide, cobalt iodides, ruthenium iodides, iron iodides and the like. Catalyst containing cobalt iodides, iron iodides and ruthenium iodides or ruthenium chlorides are preferable due to easy handling of catalyst. When the cobalt iodides, the ruthenium iodides or the iron iodides are used as components constituting the catalyst, it may be unnecessary to add additional iodine components to the catalyst system.

The amount of the cobalt compound employed is in the range of 0.1–500 mg-atom, preferably 1–50 mg-atom in terms of cobalt per 1 mol of methanol. When the amount of cobalt component is less than the lower limit mentioned above, though the reaction proceeds, the reaction speed is lowered. The use of cobalt component in an amount of more than the upper limit merely adds to production cost.

The atomic ratio of ruthenium to cobalt is in the range of 0.01 to 4, preferably 0.1 to 2. When the amount of ruthenium component is less than the lower limit mentioned above, amount of acetaldehyde and dimethoxyethane formed becomes more. When the amount of ruthenium component is more than the upper limit mentioned above, amount of ethers and methyl formate formed becomes more, and selectivity to ethanol is lowered.

The atomic ratio of iron to cobalt is in the range of 0.01 to 4, preferably 0.1 to 2. When the amount of iron component is less than the lower limit mentioned above, activity of the catalyst is lowered. When the amount of iron component is more than the upper limit mentioned above, amount of by-products formed become more and selectivity to ethanol is lowered.

The atomic ratio of iodine to cobalt is in the range of 0.05–20, preferably 0.1–10. When the amount of iodine is less than the lower limit mentioned above, the reaction speed is lowered. When the amount of iodine is more than the upper limit mentioned above, amount of acetaldehyde and dimethyl ether formed becomes more and selectivity to ethanol is lowered.

The organic solvents employed in the present invention include aromatic hydrocarbons, cyclic ethers and methyl acetate. The aromatic hydrocarbons include, for example, benzene, toluene, xylene, ethyl benzene, trimethyl benzene, methyl ethyl benzene, diethyl benzene, isopropyl benzene and the like. The cyclic ethers are represented by the formula $(R-O)_n$ wherein R is alkenyl. The cyclic ethers include, for example, tetrahydrofuran, 1,3-dioxane and 1,4-dioxane. Amount of the solvents employed may be in the range of 0.05 to 20 parts by volume, preferably 0.1 to 10 parts by volume per 1 part by volume of methanol.

It is necessary to add water to the reaction system in order to increase selectivity to neat ethanol. Amount of water employed may be in the range of 0.1–2 mol per 1 mol of methanol. When the amount of water is more than the upper limit mentioned above, amount of acetic acid and methyl acetate formed becomes more, and selectivity to ethanol is lowered.

The reaction temperature depends on the catalyst employed and other reaction conditions. In general, the temperature may be in the range of 100°–250° C., preferably 130°–200° C. Though the reaction proceeds at a temperature below 100° C., the reaction speed is low; at temperatures above 250° C. by-products forms.

The reaction pressure may be in the range of more than 50 kg/cm$^2$G, and preferably, the pressure is in the range of 100–500 kg/cm$^2$G in the practice of the present invention. Carbon monoxide and hydrogen may be used in an amount of more than the stoichiometric amount of methanol. The molar ratio of CO to H$_2$ employed may be in the range of 4:1 to 1:4, preferably 2:1 to 1:2.

Carbon monoxide and hydrogen employed in the present invention may contain argon, nitrogen, carbon dioxide, methane which are inert to the reaction. In this case, the total partial pressure of each of carbon monoxide and hydrogen is within the above reaction pressure.

According to the present invention, selectivity to ethanol is high and ethanol can be obtained under mild conditions. In addition, since instable ligands are not used, it is easy to recover the catalyst from the reaction system. Methanol containing water which is regarded to be a lower grade can be used as a starting material. A process for producing ethanol according to the present invention is useful from industrial point of view.

The present invention can be carried out either as batch process or as a continuous process.

The present invention is further illustrated by non-limiting Examples and Comparative Run.

In the following Examples and Comparative Run, reactivity of methanol, selectivity to ethanol, substantial reactivity of methanol and selectivity to realizable ethanol are expressed by the following equations:

Reactivity of methanol (%) =

$$\frac{\text{mol of CH}_3\text{OH fed} - \text{mol of unreacted CH}_3\text{OH}}{\text{mol of CH}_3\text{OH fed}} \times 100$$

Selectivity to each product (%) =

$$\frac{\text{mol of CH}_3\text{OH converted to each product}}{\text{mol of CH}_3\text{OH fed} - \text{mol of unreacted CH}_3\text{OH}} \times 100$$

Substantial reactivity of methanol (%) =

$$\frac{\begin{array}{c}\text{mol of CH}_3\text{OH fed} - \\ \text{mol of unreacted CH}_3\text{OH} - \\ \text{mol of CH}_3\text{OH converted}^{*1}\end{array}}{\text{mol of CH}_3\text{OH fed}} \times 100$$

Selectivity to realizable ethanol (%) =

$$\frac{\text{mol of neat ethanol} + \text{mol of ethanol converted}^{*2}}{\begin{array}{c}\text{mol of CH}_3\text{OH fed} - \\ \text{mol of unreacted CH}_3\text{OH} - \\ \text{mol of CH}_3\text{OH converted}\end{array}} \times 100$$

EXAMPLE 1

Into a shaking type 100 ml autoclave made of stainless steel were charged 7 gram (g) (0.2185 mol) of methanol, 12 g (0.154 mol) of benzene, 2 g (0.111 mol) of water, 0.5 g (1.6 milli mol) of cobalt (II) iodide, 0.25 g (0.81 milli mol) of iron (I) iodide and 0.2 g (0.76 milli mol) of ruthenium (III) chloride trihydrate. The autoclave was closed. Mixed gas of $H_2$ and CO (molar ratio of 2:1) was fed to pressure of 240 kg/cm$^2$G. The reaction was carried out at 150° C. for three hours.

After the reaction, the autoclave was cooled and the gas remaining inside the autoclave was discharged to atmospheric pressure. Gas Chromatograph (GC) Analysis (internal standard method) showed reactivity of methanol of 26.8% and selectivity to neat ethanol of 75.6%. Selectivity to each of the following components was as follows:

| | |
|---|---|
| dimethyl ether | 2.44% |
| acetaldehyde | 0.27% |
| methyl formate | 0.07% |
| methyl ethyl ether | 3.61% |
| diethyl ether | 0.54% |
| methyl acetate | 4.88% |
| acetic acid | 0.60% |
| ethyl acetate | 0.82% |

This shows substantial reactivity of methanol of 25.0% and selectivity to realizable ethanol of 84.3%.

EXAMPLES 2-10

The procedures of Example 1 were repeated by using components given in Table 1 and reaction conditions given in Table 1. The results are shown in Table 1.

TABLE 1

| Example | 2 | 3 | 4 | 5 | 6 |
|---|---|---|---|---|---|
| components | | | | | |
| methanol g (mol) | 7(0.2185) | 7(0.2185) | 7(0.2185) | 7(0.2185) | 7(0.2185) |
| Co component g (m mol) | $CoI_2$ 0.5(1.6) | $CoI_2$ 0.5(1.6) | $CoI_2$ 0.5(1.6) | $CoI_2$ 0.5(1.6) | $CoI_2$ 0.25(0.80) |
| Fe component g (m mol) | $FeI_2$ 0.5(1.6) | $FeI_2$ 0.75(2.4) | $FeI_2$ 0.5(1.6) | $FeI_2$ 0.25(0.81) | $FeI_2$ 0.25(0.81) |
| Ru component g (m mol) | $RuCl_3.3H_2O$ 0.2(0.76) | $RuCl_3.3H_2O$ 0.2(0.76) | $RuCl_3.3H_2O$ 0.1(0.38) | $RuCl_3.3H_2O$ 0.2(0.76) | $RuCl_3.3H_2O$ 0.1(0.38) |
| solvent I g (mol) | $C_6H_6$ 12(0.154) | $C_6H_6$ 12(0.154) | $C_6H_6$ 12(0.154) | $C_6H_6$ 12(0.154) | $C_6H_6$ 12(0.154) |
| solvent II g (mol) | — | — | — | — | — |
| water g (mol) | 2(0.111) | 2(0.111) | 2(0.111) | 2(0.111) | 2(0.111) |
| molar ratio of mixed gas ($H_2$/CO) | 2 | 2 | 2 | 3 | 2 |
| reaction condition | | | | | |
| pressure Kg/cm$^2$G | 240 | 240 | 240 | 320 | 240 |
| temp./hr °C./hr | 150/3 | 150/3 | 150/3 | 150/3 | 170/2 |
| reactivity of methanol % | 26.7 | 28.0 | 28.2 | 33.1 | 39.7 |
| substantial reactivity of methanol % | 24.8 | 26.0 | 26.3 | 29.1 | 36.3 |
| selectivity to each component (%) | | | | | |
| dimethyl ether | 1.61 | 1.04 | 1.00 | 5.19 | 2.51 |
| acetaldehyde | 0.65 | 0.54 | 0.61 | 0.23 | 0.31 |
| methyl formate | — | 0.13 | 0.13 | 0.06 | 0.09 |
| methyl ethyl ether | 4.24 | 7.02 | 5.25 | 7.96 | 8.80 |
| ethanol | 74.1 | 71.6 | 71.4 | 72.0 | 72.1 |
| diethyl ether | 0.78 | — | 0.52 | 0.27 | — |
| methyl acetate | 6.55 | 4.62 | 4.36 | 3.86 | 3.05 |
| acetic acid | — | — | — | — | — |
| n-propanol | 0.68 | 0.99 | 0.96 | 0.39 | 0.32 |
| dimethoxyethane | — | — | 0.90 | 1.22 | — |
| ethyl acetate | 0.75 | 0.09 | 0.61 | 0.23 | 0.81 |
| realizable ethanol | 83.9 | 81.4 | 81.0 | 87.4 | 84.4 |

| Example | 7 | 8 | 9 | 10 |
|---|---|---|---|---|
| components | | | | |

TABLE 1-continued

| | | | | |
|---|---|---|---|---|
| methanol g (mol) | 5(0.1561) | 7(0.2185) | 7(0.2185) | 7(0.2185) |
| Co component | CoI$_2$ | Co$_2$(CO)$_8$ | CoI$_2$ | CoI$_2$ |
| g (m mol) | 0.5(1.6) | 0.14(0.41) | 0.25(0.80) | 0.5(1.6) |
| Fe component | FeI$_2$ | FeI$_2$ | Fe(CO)$_5$ | FeI$_2$ |
| g (m mol) | 0.25(0.81) | 0.25(0.81) | 0.16(0.81) | 0.25(0.81) |
| Ru component | RuCl$_3$.3H$_2$O | RuCl$_3$.3H$_2$O | RuCl$_3$.3H$_2$O | RuI$_3$ |
| g (m mol) | 0.2(0.76) | 0.1(0.38) | 0.10(0.38) | 0.37(0.77) |
| solvent I | C$_6$H$_6$ | C$_6$H$_6$ | C$_6$H$_6$ | C$_6$H$_5$CH$_3$ |
| g (mol) | 6(0.077) | 12(0.154) | 12(0.154) | 12(0.130) |
| solvent II | dioxane | — | — | — |
| g (mol) | 6(0.068) | — | — | — |
| water g (mol) | 2(0.111) | 2(0.154) | 2(0.111) | 2(0.111) |
| molar ratio of mixed gas (H$_2$/CO) | 2 | 2 | 2 | 2 |
| reaction condition | | | | |
| pressure Kg/cm$^2$G | 240 | 240 | 240 | 240 |
| temp./hr °C./hr | 150/3 | 170/3 | 170/2 | 150/2 |
| reactivity of methanol % | 53.2 | 23.1 | 21.9 | 32.0 |
| substantial reactivity of methanol % | 49.2 | 21.2 | 20.4 | 28.8 |
| selectivity to each component (%) | | | | |
| dimethyl ether | 2.12 | 1.72 | 1.41 | 3.02 |
| acetaldehyde | 0.49 | 0.20 | — | 1.03 |
| methyl formate | 0.05 | 0.81 | 1.85 | 0.05 |
| methyl ethyl ether | 5.68 | 8.96 | 8.66 | 7.30 |
| ethanol | 71.1 | 70.6 | 70.3 | 70.4 |
| diethyl ether | 0.58 | — | 0.50 | — |
| methyl acetate | 5.92 | 2.38 | 2.38 | 4.70 |
| acetic acid | 0.45 | — | 1.24 | — |
| n-propanol | 1.26 | 1.17 | 1.24 | 0.46 |
| dimethoxyethane | — | — | — | 1.04 |
| ethyl acetate | 3.07 | — | — | 1.03 |
| realizable ethanol | 83.2 | 82.0 | 79.4 | 84.2 |

Comparative Run 1

The procedure of Example 1 was repeated except that iron iodide was not used. Gas Chromatograph (GC) Analysis (internal standard method) showed reactivity of methanol of 23.2% and selectivity to neat ethanol of 67.8%. Selectivity to each of the following components was as follows:

| | |
|---|---|
| dimethyl ether | 6.71% |
| acetaldehyde | 0.10% |
| methyl formate | 0.23% |
| methyl ethyl ether | 7.87% |
| n-propanol | 0.23% |
| methyl acetate | 4.66% |
| ethyl acetate | 0.62% |

Comparative Run 1 showed selectivity to neat ethanol lower than that of Example 1 by about 8%.

Comparative Runs 2-9

The procedures of Example 1 were repeated by using components given in Table 2 and reaction conditions given in Table 2. The results are shown in Table 2.

Comparative Runs 2, 3, 4, 5 and 9 do not employ any iron component; Comparative Runs 7 and 8 do not employ any organic solvent and Comparative Run 6 does not employ water.

TABLE 2

| Comparative Run | 2 | 3 | 4 | 5 |
|---|---|---|---|---|
| components | | | | |
| methanol g (mol) | 7(0.2185) | 7(0.2185) | 7(0.2185) | 7(0.2185) |
| Co component | CoI$_2$ | CoI$_2$ | CoI$_2$ | CoI$_2$ |

TABLE 2-continued

| | | | | |
|---|---|---|---|---|
| g (m mol) | 0.5(1.6) | 0.5(1.6) | 0.25(0.81) | 0.25(0.80) |
| Fe component (I component) | $I_2$ | $I_2$ | — | $I_2$ |
| g (m mol) | 0.21(0.81) | 0.41(1.6) | — | 0.21(0.81) |
| Ru component | $RuCl_3.3H_2O$ | $RuCl_3.3H_2O$ | $RuCl_3.3H_2O$ | $RuCl_3.3H_2O$ |
| g (m mol) | 0.2(0.76) | 0.2(0.76) | 0.1(0.38) | 0.1(0.38) |
| solvent I | $C_6H_6$ | $C_6H_6$ | $C_6H_6$ | $C_6H_6$ |
| g (mol) | 12(0.154) | 12(0.154) | 12(0.154) | 12(0.154) |
| solvent II | — | — | — | — |
| g (mol) | — | — | — | — |
| water | 2(0.111) | 2(0.111) | 2(0.111) | 2(0.111) |
| molar ratio of mixed gas ($H_2$/CO) | 2 | 2 | 2 | 2 |
| reaction condition | | | | |
| pressure Kg/cm$^2$G | 240 | 240 | 240 | 240 |
| temp./hr °C./hr | 150/3 | 150/3 | 170/2 | 170/2 |
| reactivity of methanol % | 33.0 | 42.5 | 35.4 | 48.0 |
| substantial reactivity of methanol % | 28.6 | 32.1 | 30.9 | 41.3 |
| selectivity of each component (%) | | | | |
| dimethyl ether | 7.31 | 19.1 | 5.57 | 7.68 |
| acet-aldehyde | 0.22 | 0.06 | 0.14 | 0.21 |
| methyl formate | 0.05 | 0.04 | 0.35 | 0.04 |
| methyl ethyl ether | 7.69 | 8.01 | 11.0 | 9.17 |
| ethanol | 64.5 | 47.8 | 63.7 | 62.3 |
| diethyl ether | — | — | — | — |
| methyl acetate | 4.37 | 2.63 | 2.74 | 3.41 |
| acetic acid | — | 0.26 | — | — |
| n-propanol | 0.22 | 0.17 | 0.60 | 0.65 |
| dimethoxy ethane | — | — | — | — |
| ethyl acetate | 0.75 | 0.58 | 0.54 | 0.89 |
| realizable ethanol | 79.7 | 69.1 | 79.8 | 78.6 |

| Comparative Run | 6 | 7 | 8 | 9 |
|---|---|---|---|---|
| components | | | | |
| methanol g (mol) | 7(0.2185) | 17.5(0.5462) | 7(0.2185) | 7(0.2185) |
| Co component | $CoI_2$ | $CoI_2$ | $CoI_2$ | $Co_2(CO)_8$ |
| g (m mol) | 0.5(1.6) | 1.25(4.0) | 0.5(1.6) | 0.14(0.41) |
| Fe component (I component) | $FeI_2$ | $FeI_2$ | $FeI_2$ | — |
| g (m mol) | 0.25(0.81) | 0.63(2.0) | 0.25(0.81) | — |
| Ru component | $RuCl_3.3H_2O$ | $RuCl_3.3H_2O$ | $RuCl_3.3H_2O$ | $RuCl_3.3H_2O$ |
| g (m mol) | 0.2(076) | 0.5(1.91) | 0.2(0.76) | 0.1(0.38) |
| solvent I | $C_6H_6$ | — | n-hexane | $C_6H_6$ |
| g (mol) | 12(0.154) | — | 12(0.139) | 12(0.154) |
| solvent II | — | — | — | — |
| g (mol) | — | — | — | — |
| water | — | 5(0.278) | 2(0.111) | 2(0.111) |
| molar ratio of mixed gas ($H_2$/CO) | 2 | 2 | 2 | 2 |
| reaction condition | | | | |
| pressure Kg/cm$^2$G | 240 | 240 | 240 | 240 |
| temp./hr °C./hr | 150/3 | 150/3 | 150/3 | 170/3 |
| reactivity of methanol % | 42.2 | 43.4 | 29.6 | 12.0 |
| substantial reactivity of methanol % | 36.5 | 27.7 | 24.3 | 8.5 |
| selectivity to each component | | | | |

TABLE 2-continued

| (%) | | | | |
|---|---|---|---|---|
| dimethyl ether | 2.60 | 26.1 | 4.96 | 3.65 |
| acetaldehyde | 0.43 | 0.05 | 0.24 | 1.91 |
| methyl formate | — | 0.04 | 0.12 | 17.1 |
| methyl ethyl ether | 26.0 | 8.50 | 7.36 | 1.40 |
| ethanol | 53.8 | 25.8 | 51.1 | 29.7 |
| diethyl ether | — | 0.36 | — | 0.23 |
| methyl acetate | 1.08 | 11.6 | 18.0 | 1.81 |
| acetic acid | — | 0.11 | — | — |
| n-propanol | 0.22 | 0.74 | 0.24 | 2.65 |
| dimethoxyethane | — | — | — | 10.6 |
| ethyl acetate | — | 1.71 | 1.86 | — |
| realizable ethanol | 78.8 | 49.1 | 68.0 | 51.1 |

What is claimed is:

1. A process for producing ethanol which comprises reacting methanol, carbon monoxide, and hydrogen in the presence of:
   (a) a catalyst consisting essentially of a cobalt component, said cobalt component selected from the group consisting of cobalt iodides, cobalt bromides, cobalt chlorides, cobalt oxides, cobalt carbonates, cobalt formates, cobalt acetates, cobalt naphthenates, cobalt carbonyls and cobalt acetylacetonates; an iron component, said iron component selected from the group consisting of iron iodides, iron chlorides, iron oxides, iron acetates, iron acetylacetonates, and iron carbonyls; a ruthenium component, said ruthenium component selected from the group consisting of ruthenium iodides, ruthenium chlorides, ruthenium bromides, ruthenium hydroxides, ruthenium acetates, and ruthenium carbonyls; and an iodine component said iodine component selected from the group consisting of iodine, hydrogen iodide, methyl iodide, sodium iodide, potassium iodide, calcium iodide, lithium iodide, cobalt iodides, ruthenium iodides, and iron iodides;
   (b) at least one organic solvent; and
   (c) water;
   said catalyst consisting essentially of from about 0.1 to about 500 milligram atoms of cobalt per mol of methanol, from about 0.1 to about 4 atoms of iron component per mol of methanol; from about 0.01 to about 4 atoms of ruthenium per atom of cobalt, and from about 0.05 to about 20 atoms of iodine per atom of cobalt.

2. The process as defined in claim 1 wherein the cobalt component is cobalt (II) iodide.

3. The process as defined in claim 1 wherein the iron component is iron (II) iodide.

4. The process as defined in claim 1 wherein the ruthenium component is $RuCl_3 \cdot 3H_2O$.

5. The process as defined in claim 4 wherein the solvent is benzene.

6. The process as defined in claim 4 wherein solvent is used in an amount of 0.05–20 parts by volume per 1 part by volume of methanol.

7. The process as defined in claim 1 wherein carbon monoxide and hydrogen are used in an amount of more than the stoichiometric amount of methanol.

8. The process as defined in claim 1 wherein the reaction pressure is in the range of 100–500 kg/cm$^2$G.

9. The process as defined in claim 1 wherein the reaction temperature is in the range of 100°–250° C.

10. The process as defined in claim 1 wherein the amount of water is in the range of 0.1–2 mol per 1 mol of methanol.

* * * * *